(12) United States Patent
Bzdusek et al.

(10) Patent No.: US 9,498,645 B2
(45) Date of Patent: Nov. 22, 2016

(54) DOSE DEFORMATION ERROR CALCULATION METHOD AND SYSTEM

(71) Applicant: KONINKLIJKE PHILIPS N.V., Eindhoven (NL)

(72) Inventors: Karl Antonin Bzdusek, Madison, WI (US); Mark David Wiesmeyer, Fitchburg, WI (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 82 days.

(21) Appl. No.: 14/416,065

(22) PCT Filed: Jul. 9, 2013

(86) PCT No.: PCT/IB2013/055632
§ 371 (c)(1),
(2) Date: Jan. 21, 2015

(87) PCT Pub. No.: WO2014/016720
PCT Pub. Date: Jan. 30, 2014

(65) Prior Publication Data
US 2015/0174428 A1    Jun. 25, 2015

Related U.S. Application Data

(60) Provisional application No. 61/676,362, filed on Jul. 27, 2012.

(51) Int. Cl.
G06K 9/00 (2006.01)
A61N 5/10 (2006.01)
G06T 7/00 (2006.01)
(Continued)

(52) U.S. Cl.
CPC ............ *A61N 5/1037* (2013.01); *A61B 6/035* (2013.01); *A61B 6/469* (2013.01); *A61N 5/1031* (2013.01); *A61N 5/1071* (2013.01); *G06T 7/003* (2013.01); *G06T 7/204* (2013.01); *A61N 2005/1072* (2013.01); *G06T 2207/10081* (2013.01)

(58) Field of Classification Search
CPC .................. A61B 6/035; A61B 6/469; A61N 2005/1072; A61N 5/1031; A61N 5/1037; A61N 5/1071; G06T 2207/10081; G06T 7/003; G06T 7/204
USPC ....................................................... 382/128
See application file for complete search history.

(56) References Cited

U.S. PATENT DOCUMENTS

| 7,693,257 B2 * | 4/2010 | Allison .................. A61N 5/103 378/108 |
| 7,708,682 B2 | 5/2010 | Pekar et al. |

(Continued)

OTHER PUBLICATIONS

Bharat, S., et al.; Motion-compensated estimation of delivered dose during external beam radiation therapy: Implementation in Philips' Pinnacle3 treatment planning system; 2012; Med. Phys.; 39(1)437-443.

(Continued)

*Primary Examiner* — Tom Y Lu (57) ABSTRACT

A method and system for determining a radiation dose transformation error are provided, wherein there is a deformation in one or more imaged structures as recorded by at least one fixed image data set and at least one moving image data set. Corresponding landmark points in the fixed image and in the moving image are automatically or semi-automatically identified.

17 Claims, 5 Drawing Sheets

(51) Int. Cl.
  *G06T 7/20*  (2006.01)
  *A61B 6/03*  (2006.01)
  *A61B 6/00*  (2006.01)

(56) References Cited

U.S. PATENT DOCUMENTS

| | | | |
|---|---|---|---|
| 8,073,102 B2 | 12/2011 | Fallone et al. | |
| 8,492,735 B2* | 7/2013 | Brand | A61N 5/103 250/492.1 |
| 8,509,383 B2* | 8/2013 | Lu | A61N 5/1049 378/108 |
| 2009/0187422 A1 | 7/2009 | Kaus et al. | |
| 2010/0086183 A1 | 4/2010 | Vik et al. | |

OTHER PUBLICATIONS

Murphy, M. J., et al.; A method to estimate the effect of deformable image registration uncertainties on daily dose mapping; 2012; Med. Phys.; 39(2)573-580.

Saleh-Sayah, N. K., et al.; A distance to dose difference tool for estimating the required spatial accuracy of a displacement vector field; 2011; Med. Phys.; 38(5)2318-2323.

* cited by examiner

DOSE DEFORMATION ERROR CALCULATION METHOD AND SYSTEM

CROSS REFERENCE TO RELATED APPLICATIONS

This application is a national filing of PCI application Serial No. PCT/IB2013/055632, filed Jul. 9, 2013, published as WO 2014/015720 A2 on Jan. 30, 2014, which claims the benefit of U.S. provisional application Ser. No. 61/676,362 filed Jul. 27, 2012, which is incorporated herein by reference.

The present application relates generally to a method and system for radiation therapy planning. Radiation therapy is the process by which trained medical professionals plan and execute a delivery of ionizing radiation to a patient. The goal of radiation delivery can widely vary. Very commonly this therapy is used to treat a disease such as cancer by ionizing the diseased tissue, thereby destroying the diseased tissue. A central goal of radiation therapy planning is to control the radiation delivery to maximize radiation exposure to the target area within the patient's body (i.e., diseased tissue) while minimizing radiation exposure to non-target areas within the patient's body (i.e., healthy tissue).

As commonly implemented, radiation therapy begins with a detailed three-dimensional imaging scan of the patient's body, such as a computed tomography (CT) scan. A trained medical professional often specifies several characteristics of a radiation therapy plan based on the imaging data. For example, using the imaging data, the medical professional can identify specific target and non-target areas within the patient's body. The professional can further specify a minimum radiation dosage to be delivered to the target area (i.e., enough to destroy the diseased tissue), a maximum radiation dosage to be delivered to various non-target areas (i.e., to limit damage to healthy tissue), and several other desired characteristics of a radiation therapy.

In many situations, the patient to be treated with radiation therapy will have already undergone one or more prior radiation therapy treatments. It is then desirable for the medical professional to know the already-delivered radiation dosages to various regions of the patient's body, to better prepare the currently proposed treatment. This can be particularly difficult in situations where the patient has already received more than one radiation therapy delivery, especially in clinical contexts where high degrees of accuracy are required. Determining already-delivered radiation dosages can also be useful even during a single radiation delivery session to help maintain quality control of the radiation delivery, to compensate for patient motion during delivery, and perhaps for other reasons.

The radiation dosage calculation begins with imaging data which identifies the radiation dosage delivered to the patient in each one of the previous radiation therapy sessions. This imaging data is stored on a 3D voxel-by-voxel basis or a 2D pixel-by-pixel basis. The following discussion assumes the imaging data is three-dimensional, but the concepts apply equally well to the two-dimensional context.

The imaging data usually includes, for each prior radiation delivery session, at least two data points for each voxel. The first data point is a structural data point, representing a relative density of the structure located at the voxel relative to other structures in the imaging data. Thus, voxels representing a dense structure typically appear darker in the imaging data than voxels representing less dense structures. Contiguous voxel collections of similar density values represent the same structure. In this way, the imaging data shows the medical professional the locations and orientations of bone (high density), organs such as the heart or liver (medium density), interstitial areas (low density), and other regions inside the patient's body. The second voxel data point is a radiation dosage data point, representing the radiation dosage which was delivered to the voxel's point in space by the prior radiation delivery session. In this way, for each prior radiation delivery session, the imaging data reflects a structural voxel grid and a radiation dosage voxel grid. When combined, these two grids show the medical professional the radiation dosage distribution delivered to the patient in the previous radiation therapy session.

Such imaging data on its own can obviously be useful in planning future radiation delivery sessions. Its usefulness can be enhanced, however, if the radiation dosage values can be "transformed" or "mapped" to a current imaging data set of the patient being used to plan the next radiation delivery therapy. That is, in the time which has passed between the previous radiation delivery or deliveries and the radiation delivery currently being planned, the locations and orientations of the patient's internal organs will have changed. Such movement is caused, for example, by the patient's breathing, heart beating, weight gain or loss, digestive processes, and other physiological processes. In addition, between radiation delivery sessions the size of the targeted tumor or other target region may very well have either shrunk in response to the prior treatment, or grown despite the treatment. The deformations resulting from these and other considerations can often be significant, especially given the high accuracy of the imaging data being used. Thus, the goal of the transformation process is to identify, on a voxel-by-voxel basis, the difference in position of anatomically "corresponding" voxels between the two imaging data sets. Transformation difficulties caused by movement or other deformations are multiplied when there is more than one prior radiation delivery session which must be combined in order to gain a full understanding of the patient's radiation profile.

There are several such transformation processes known in the art, such as a relatively simple rigid transformation, and more complex deformable image transformations which employ a displacement vector field (DVF). If the deformation or differences between the two imaging data sets is significant, then it is more accurate to employ a deformable DVF image transformation. The same DVF transform can be applied to both grids of an imaging data set: the structural grid and the radiation dosage grid. Thus, appropriate DVF transforms can be applied to two or more different data sets in order to transform each of the data sets to a common coordinate frame of reference.

At least two different kinds of errors can arise during the transformation warping process: errors associated with computing the DVF ("DVF computation errors"), and errors associated with applying the DVF to the radiation dose grids ("dose warping errors"). There are known methods to calculate each type of error, separately. Geometric DVF computation errors can be determined, for example, using methods such as measuring the Dice similarity score or Housdorf distance to agreement of propagated contours against "truth" contours. Also, methods for determining the spatial accuracy required from a DVF throughout an image volume based on dose gradients have been described. See, e.g., Nahla K. Saleh-Sayah et al., "A Distance to Dose Difference Tool for Estimating the Required Spatial Accuracy of a Displacement Vector Field", *Medical Physics*, vol. 38, issue 5, pages 2318-2323 (May 2011). Dose warping errors can be determined, for example, by warping both a dose grid and regions of interest and computing dose volume histograms (DVH)

for the regions of interest before and after warping. Then, the difference in DVHs can provide an indication of which structures may have more dose warping error. A more global approach based on the same concept can be found in Martin J. Murphy et al., "A Method to Estimate the Effect of Deformable Image Registration Uncertainties on Daily Dose Mapping", *Medical Physics*, vol. 39, issue 2, pages 573-580 (February 2012).

Determining the overall dose transformation error, combining both the DVF computation errors and the dose warping errors in an efficient manner, has proven difficult and elusive. The present disclosure offers methods for calculating an overall dose transformation error. The errors may correspond either to transformation warping of one single radiation dose grid, or to dose accumulated using more than one transformed radiation dose grid.

A method and system for determining a radiation dose transformation error are provided, wherein there is a deformation in one or more imaged structures as recorded by at least one fixed image data set and at least one moving image data set. Corresponding landmark points in the fixed image and in the moving image are automatically or semi-automatically identified. A fixed image radiation dose grid and a moving image radiation dose grid are obtained, wherein the moving image radiation dose grid comprises actual moving image point doses representing radiation dose levels at the landmark points in the moving image radiation dose grid. A transformation matrix between the fixed image and the moving image is determined, and applied to the moving image data set to generate a warped radiation dose grid. The warped radiation dose grid contains warped point doses representing radiation dose levels in the warped radiation dose grid at the landmark points in the fixed image radiation dose grid. A difference between the actual point dose and the warped point dose at corresponding landmark points is determined in order to generate dose errors.

In one implementation, these methods may be at least automated or semi-automated to identify corresponding landmark points between the fixed image data set and the moving image data set. A first region of interest in one of the fixed image data set and the moving image data set, and a second region of interest in the other of the fixed image data set and the moving image data set, are identified so that the first region of interest corresponds anatomically to the second region of interest. A first surface mesh is generated to approximate the first region of interest, and a second surface mesh is generated to approximate the second region of interest, wherein the first and second surface meshes comprise an equal number of vertices. At least one vertex in the first region of interest and at least one vertex in the second region are identified as anatomically corresponding landmark points.

Radiation therapy planning systems incorporating the methods are also provided.

Numerous advantages and benefits will become apparent to those of ordinary skill in the art upon reading the following detailed description of several embodiments. The invention may take form in various components and arrangements of components, and in various process operations and arrangements of process operations. The drawings are only for the purpose of illustrating many embodiments and are not to be construed as limiting the invention.

The present disclosure describes methods and systems for planning a radiation therapy treatment using a radiation therapy delivery system in conjunction with any one or more of various imaging system modalities. Such imaging system modalities include, for example, computed tomography (CT) imaging, cone beam CT, other x-ray based imaging, ultrasound imaging, magnetic resonance imaging (MRI), PET, and the like.

Figure 1:
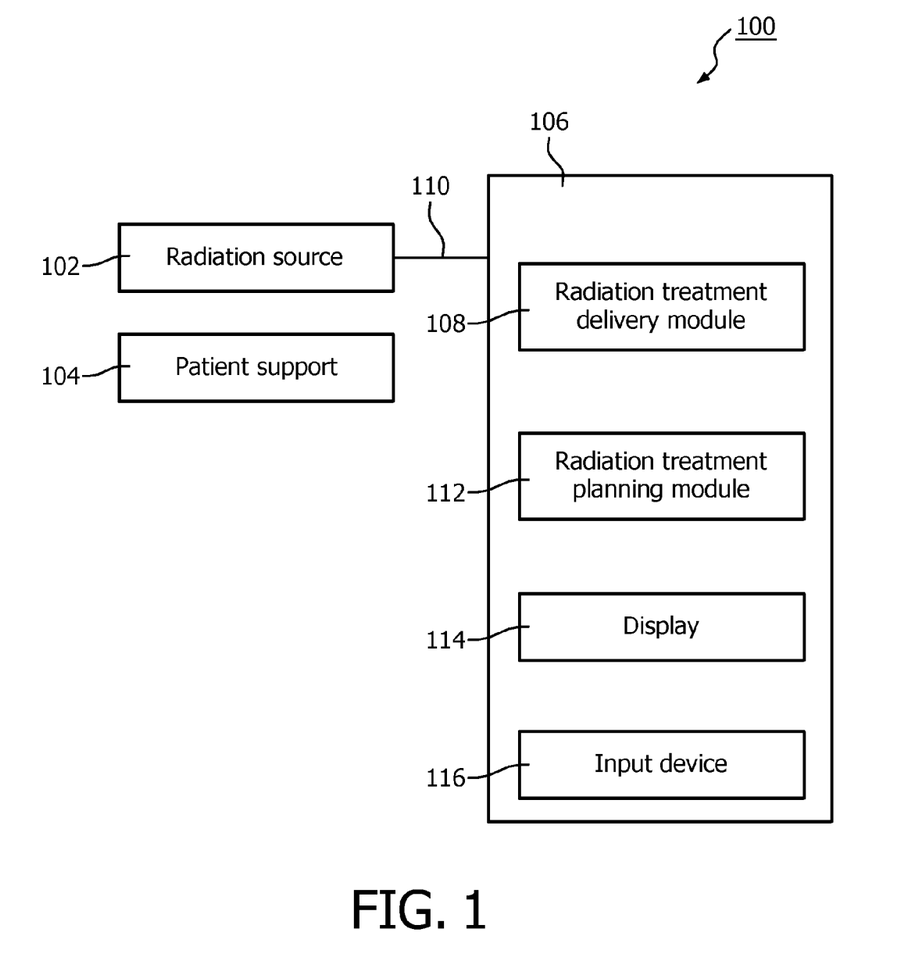
FIG. 1 schematically illustrates a typical radiation therapy delivery system 100.

A typical radiation therapy system 100 is schematically illustrated in FIG. 1. Thus, the system 100 includes a radiation source 102 for directing and providing radiation to designated target region(s) within a patient disposed on a support 104. The radiation source 102 may be, for example, an x-ray source or some other suitable source for providing radiation for radiation therapy. The radiation source 102 is mounted on a movable support structure (not shown) so that it may be maneuvered to various positions and orientations around the patient for directing and providing radiation to the designated target region within the patient. The target region may be, for example, a tumor in the patient.

The radiation therapy system 100 additionally includes a control console 106. The control console 106 has a radiation treatment delivery module 108 to move and operate the radiation source 102 through a wired or wireless communication link 110. The control console 106 includes one or more processors and a memory for performing those operations and other tasks. Thus the functions described herein can be performed as software logic. "Logic," as used herein, includes but is not limited to hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), or other programmed logic device. Logic may also be fully embodied as software.

"Software," as used herein, includes but is not limited to one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, and/or the desires of a designer/programmer or the like. The Logic of the radiation treatment delivery module 108 may most easily be embodied as part of a software package.

The methods and systems described herein can be implemented on a variety of platforms including, for example, networked control systems and stand-alone control systems. Additionally, the logic shown and described herein preferably resides in or on a computer readable medium. Examples of different computer readable media include Flash Memory, Read-Only Memory (ROM), Random-Access Memory (RAM), programmable read-only memory (PROM), electrically programmable read-only memory (EPROM), electrically erasable programmable read-only memory (EEPROM), magnetic disk or tape, optically readable mediums including CD-ROM and DVD-ROM, and others. Still further, the processes and logic described herein can be merged into one large process flow or divided into many sub-process flows. The order in which the process flows herein have been described is not critical and can be rearranged while still accomplishing the same results. Indeed, the process flows described herein may be rearranged, consolidated, and/or re-organized in their implementation as warranted or desired.

The control console 106 further includes a radiation treatment planning module 112 with one or more processors and a memory. The radiation treatment planning module 112 includes tools to create and/or import regions of interest, and to compute and/or import radiation dose grids. The module 112 is able to load multiple imaging data sets, and the regions of interest and radiation dose grids may be associated with multiple imaging data sets. The control console 106 has a display 114 and an input device 116 such as a mouse and/or keyboard for user interaction with the radiation treatment delivery module 108 and the radiation treatment planning module 112.

The exemplary console 106 incorporates both a radiation treatment delivery module 108 and a radiation treatment planning module 112. In other embodiments, the two modules 108 and 112 may be incorporated in different consoles which are physically separated from each other. Thus, in such embodiments, the radiation planning module 112 is used to generate a radiation delivery plan. The generated plan may then be stored into memory and transferred to the radiation delivery module 108 for implementation at a later time.

Figure 2:
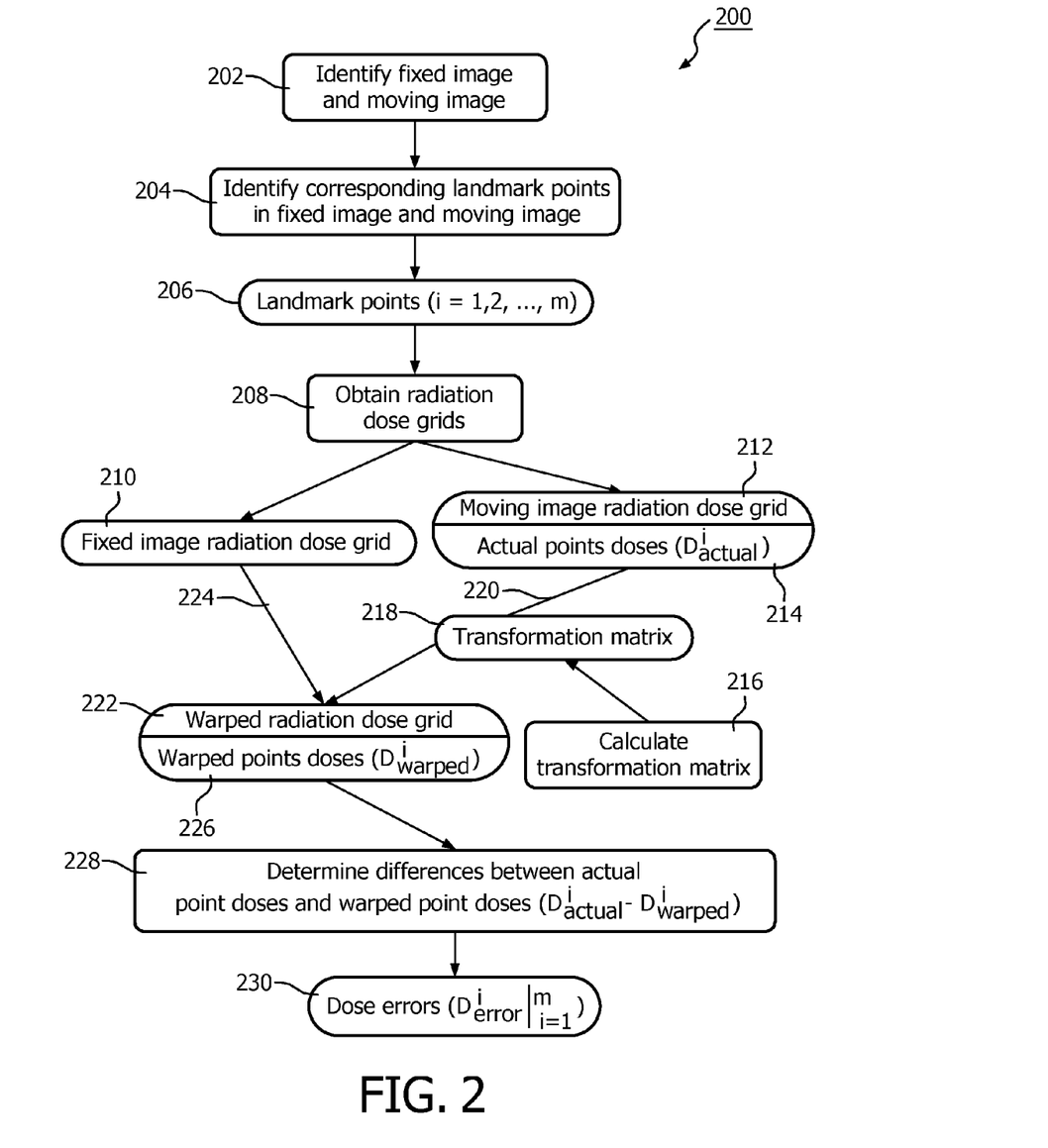
FIG. 2 illustrates a method 200 for determining an overall dose transformation error due to transformation warping of one single radiation dose grid.

FIG. 2 illustrates a method 200 for determining an overall dose transformation error due to the transformation warping of one single radiation dose grid. The method 200 may be implemented by a radiation treatment system, such as the module 112. The illustrated exemplary method 200 contains several steps. Further embodiments of a suitable method for determining an overall dose transformation error may include other additional steps, or omit one or more of the steps in the illustrated method 200. Also, the order in which the process flows herein have been described is not critical and can be rearranged while still accomplishing the same results. Thus the process flows described herein may be rearranged, consolidated, and/or re-organized in their implementation as warranted or desired.

In step 202 of the method 200, two images of the same region(s) are chosen, wherein there is deformation of the imaged structure(s) between the two images. In most cases, the two images will be of the same patient taken at different times. However, in some cases, the two images may be of the same region(s) in different patients. One of the two images is identified as the "fixed" image data set, and the other of the two images is identified as the "moving" or "deforming" image data set. The subsequent steps of the process 200 then determine the overall error in transforming radiation dosages from the moving image frame of reference to the fixed image frame of reference.

In step 204 of the method 200, corresponding landmark points 206 in the fixed image and in the moving image are identified. In one implementation, the corresponding landmark points are identified manually by a user interacting with a display 114 of a radiation therapy planning system 112. The interaction may be performed, for example, with a mouse or other pointer device. When performed entirely manually, however, this step 204 can be tedious and difficult. It can take a significant amount of time, such as a few hours, to manually identify a reasonably large sample of corresponding landmark points 206 to characterize the dose transformation errors. Various automated or semi-automated processes for identifying 204 corresponding landmark points 206 in the fixed image and in the moving image are therefore provided below. Regardless of the specific implementation, the landmark identification step 204 generates m landmark points in each of the fixed and moving images, where m is an integer greater than 0. Each one of the m landmark points 206 in the fixed image corresponds to one of the m landmark points 206 in the moving image.

In step 208 of the method 200, the radiation dose grids corresponding to the fixed image and to the moving image are obtained. If the raw imaging data has already been processed to generate the radiation dose grids, they may simply be uploaded. If the raw imaging data is unprocessed, it may be processed to compute the radiation dose grids. This step 208 results in a fixed image radiation dose grid 210 and a moving image radiation dose grid 212. The moving image radiation dose grid 212 includes at least the radiation dose levels at the landmark points 206 in the grid 212, which are referred to herein as the "actual point dose" values 214. This set of dose values may thus be represented by the short-hand $D_{actual}^i$, wherein "i" is an index running from 1 through m.

In step 216 of the method 200, a transformation matrix 218 between the fixed image data set and the moving image data set is calculated. There are several such transformation processes known in the art, such as rigid transformations and deformable transformations.

In step 220 of the method 200, the transformation matrix 218 is applied to the moving image radiation dose grid 212 to map the grid 212 to the spatial coordinate frame of the fixed image data set. This results in a transformation warped radiation dose grid 222. In step 224, the radiation dose in the warped radiation dose grid 222 is determined at each landmark point 206 of the fixed image radiation dose grid 210. These doses are referred to herein as the "warped point dose" values 226. This set of dose values may thus be represented by the short-hand $D_{warped}^i$.

In step 228 of the method 200, the difference between the actual point dose $D_{actual}^i$ and the warped point dose $D_{warped}^i$ is determined for each one of the m landmark points 206. This calculation results in a set of "dose errors" 230, with one error value corresponding to each one of the m landmark points 206 of the fixed radiation dose grid 210. This set of dose errors may thus be represented by the short-hand $D_{error}^i$, wherein $$D_{error}^i|_{i=1}^m = D_{actual}^i - D_{warped}^i.$$

The set of dose errors 230 may then be further manipulated, and/or visualized, in any one of many different manners in order to characterize the overall dose transformation error of the transformation matrix 218 operating on the moving image data set.

For example, from a manipulation standpoint, the dose errors 230 may be statistically analyzed to produce a composite dose error value which is representative of the set 230 as a whole in some manner. One of ordinary skill in the art will know of several such statistical processes. For example, depending on the context, any one or more of the maximum dose error, the minimum dose error, the average dose error, the median dose error, the standard deviation of the dose errors, and the like may be useful. In addition to such efforts which seek to describe the magnitude and numerical distribution of the dose errors, additional techniques may be applied to analyze their spatial distribution. Thus, a center of mass of the dose errors 230 may for example be generated, which would suggest the location in the imaging data which is most likely to suffer from dose transformation errors. In another example, distance to agreement algorithms may be applied to the dose errors 230 to generate distance metrics, which may be used to determine the nearest warped point dose $D_{warped}^{i}$ to a given actual point dose $D_{actual}^{i}$.

These and other statistical manipulations may be applied to the entire set of dose errors 230. They may also be applied to a subset of the dose errors 230 which is of particular interest to the investigator. Subsets may be determined for example as corresponding to regions of interest. They may alternatively or additionally be determined by applying threshold values to the dose errors 230, for example to limit the analysis to the largest fifty percent of dose errors.

From a visualization standpoint, the results of the manipulations may be illustrated on a display 114 of the radiation treatment planning system 112 in any useful format. The visualization may comprise, for example, known methods of displaying statistical results such as histograms, pie charts, scatter charts, and the like. The visualization may also take the form of a pictorial representation of the structural distribution of the dose errors 230.

For example, a dose error distribution map may be generated. In a first implementation, different colors are assigned to different ranges of dose errors 230, reflecting the magnitude and perhaps also the direction (positive or negative) of the dose errors 230. In a second implementation, arrows instead of colors may be used wherein the magnitude of the dose error 230 is indicated by the length of the arrow and the direction of the dose error 230 is indicated by the direction of the arrows. These colors or arrows are then shown on a display 114, in the structural orientation of the fixed image radiation dose grid 210. Perhaps the dose errors 230 are shown only if a user points to or hovers over a particular voxel on the display 114 with an input device 116.

Other visualization techniques may be employed as well. Isodose-error lines can be generated to connect dose errors which are similar in magnitude, similar to isodose lines in standard radiation dosage image data sets. Also, the dose errors 230 corresponding to the warped radiation dose grid 222 might be interpolated or extrapolated in any known manner to generate a continuous distribution from the discontinuous distribution of the dose errors 230 themselves.

The method 200 determines an overall dose transformation error due to the transformation warping of one single moving image radiation dose grid 212 to another frame of reference. Most typically, that other frame of reference will correspond to another radiation dose grid, identified above as the fixed image radiation dose grid 210. Thus, direct application of the method 200 typically involves one single warped dose and one fixed dose. In some situations, however, it will be desirable to transform more than one radiation dose grid to the common frame of reference. Such transformations result in more than one warped dose grid. In that case, the method 200 may be applied separately to each one of the transformed data sets. In each application, the fixed image data set corresponds to the common frame of reference, and the moving image data set corresponds to one of the imaging data sets to be transformed to the common frame of reference. In this way, the method 200 produces separate overall dose transformation errors 230 for each warped dose.

Figure 3A:
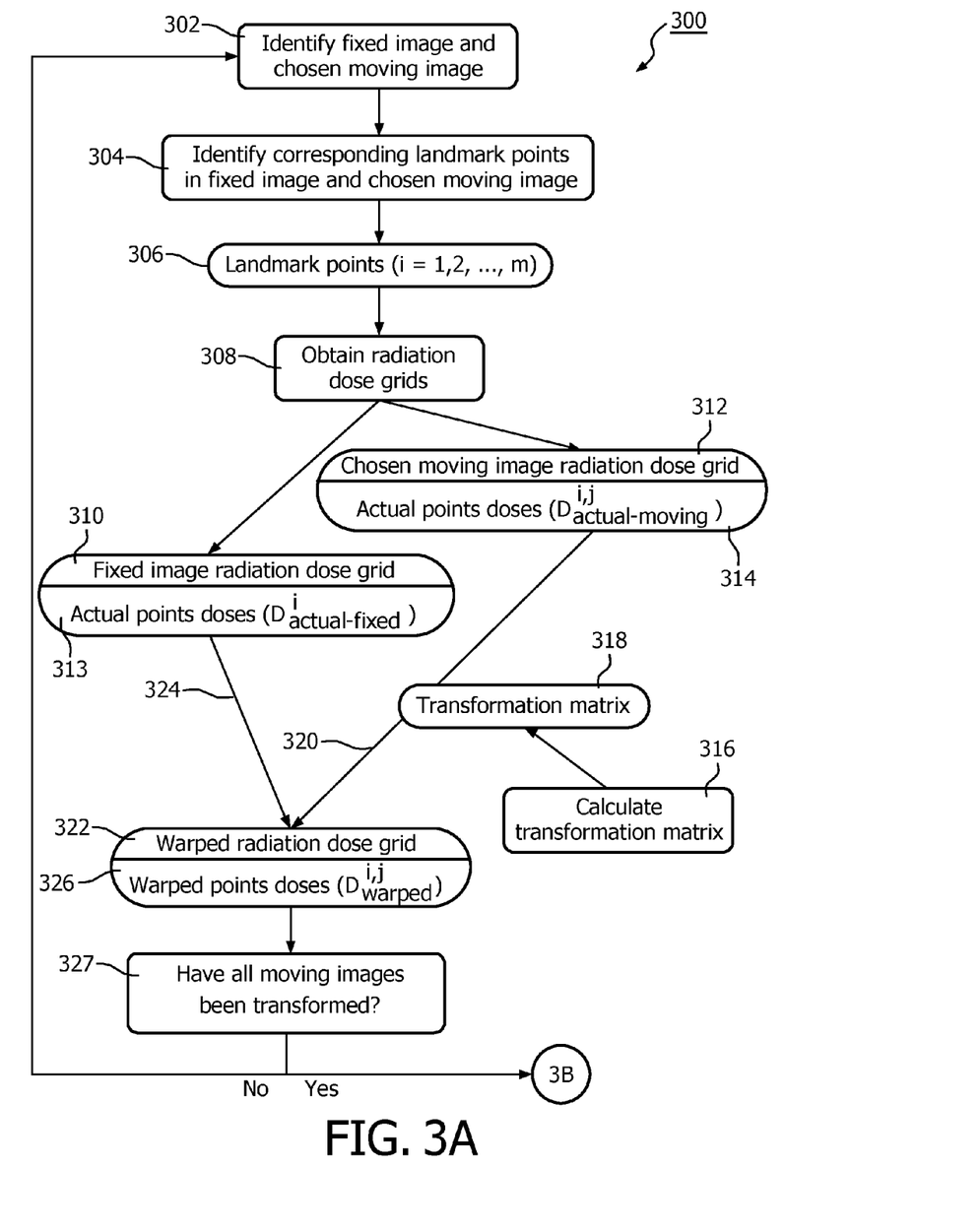
FIGS. 3A and 3B illustrate a method 300 for determining an overall dose transformation error due to the accumulated transformation warping of more than one radiation dose grid.
Figure 3B:
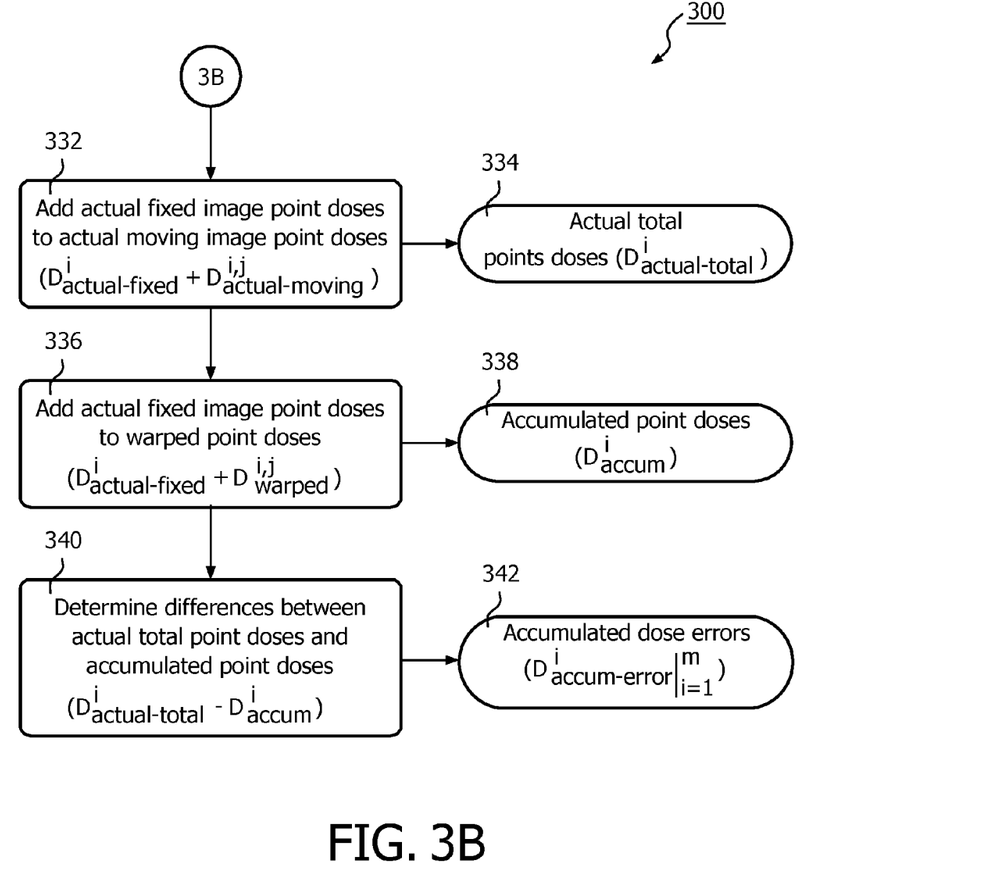

It will often be useful, however, to determine an overall dose transformation error due to the accumulated transformation warping of more than one radiation dose grid to a common frame of reference. The method 300 illustrated in FIGS. 3A and 3B is such a method. The method 300 determines an overall dose transformation error due to the accumulated transformation warping of n radiation dosage image data sets to a common frame of reference, wherein n is an integer greater than 1. The method 300 may be implemented by a radiation treatment planning system, such as the module 112. The illustrated exemplary method 300 contains several steps. Further embodiments of a suitable method for determining an overall dose transformation error may include other additional steps, or omit one or more of the steps in the illustrated method 300. Also, the order in which the process flows herein have been described is not critical and can be rearranged while still accomplishing the same results. Thus the process flows described herein may be rearranged, consolidated, and/or re-organized in their implementation as warranted or desired.

In step 302 of the method 300, one of the n radiation dosage image data sets is chosen to be transformed to a fixed image frame of reference. The chosen image data set becomes the "moving" or "deforming" image data set in steps 304 through 312 of the method 300. In most cases, the fixed and moving images will be of the same patient taken at different times. However, in some cases, the two images may be of the same region(s) in different patients.

Steps 304 through 326 of the method 300 are then identical to the steps 204 through 226 of the method 200, respectively, as applied to the moving image data set chosen in step 302. Therefore, a detailed discussion of these steps and their results in the method 300 is omitted here. In this way, the step 308 results in a fixed image radiation dose grid 310 and a moving image radiation dose grid 312. The fixed image radiation dose grid 310 includes at least the radiation dose levels at the landmark points 306 in the grid 310, which are referred to herein as the "actual fixed image point dose" values 313. This set of dose values may thus be represented by the short-hand $D_{actual-fixed}^{i}$, wherein "i" is an index running from 1 through m, the number of landmark points 306.

The chosen moving image radiation dose grid 312 similarly includes at least the radiation dose levels at the landmark points 306 in the grid 312, which are referred to herein as the "actual moving image point dose" values 314. This set of dose values may thus be represented by the short-hand $D_{actual-moving}^{i,j}$. In that description, "j" is an index running from 1 through n, to indicate which one of the n moving image data sets was chosen in step 302.

In step 316 of the method 300, a transformation matrix 318 between the fixed image data set and the chosen moving image data set is calculated. There are several such transformation processes known in the art, such as rigid transformations and deformable transformations.

In step 320 of the method 300, the transformation matrix 318 is applied to the chosen moving image radiation dose grid 312 to map the grid 312 to the spatial coordinate frame of the fixed image set. This results in a transformation warped radiation dose grid 322. In step 324, the radiation dose in the warped radiation dose grid 322 is determined at each landmark point 306 of the fixed image radiation dose grid 310. These doses are referred to herein as the "warped point dose" values 326. This set of values may thus be represented by the short-hand $D_{warped}^{i,j}$.

In step 327 of the method 300, a determination is made whether each one of the n radiation dosage image data sets has been processed through the steps 302 through 326. If not, the process 300 returns back to step 302 and chooses another one of the n radiation dosage image data sets to be transformed to the fixed image frame of reference. This new image data set becomes the chosen "moving" or "deforming" image data set in steps 304 through 326 of the method 300. Once the step 327 determines that each one of the n radiation dosage image data sets has been processed through the steps 302 through 326, the method 300 turns to step 332 which is shown in FIG. 3B.

In step 332 of the method 300, for each one of the m landmark points 306, the actual fixed image point doses $D_{actual-fixed}^i$ are added to the actual moving image point doses $D_{actual-moving}^{i,j}$. This step 332 results in a set of "actual total point dose" values 334, or $D_{actual-total}^i$, with one actual total point dose value corresponding to each one of the m landmark points 306:

$$D_{actual-total}^i|_{i=1}^m = D_{actual-fixed}^i + \Sigma_{j=1}^n D_{actual-moving}^{i,j}$$

In that expression, the first term on the right represents the actual radiation dose at the ith landmark point 306 in the fixed image data set. The second term on the right represents the summation of the actual radiation doses at the ith landmark point 306 in the n moving image data sets 312.

In step 336 of the method 300, for each one of the m landmark points 306 in the fixed image radiation dose grid 310, the actual fixed image point doses $D_{actual-fixed}^i$ are added to the warped point doses $D_{warped}^{i,j}$. This step 336 results in a set of "accumulated point dose" values 338, or $D_{accum}^i$, with one accumulated point dose value corresponding to each one of the m landmark points 306 in the fixed image radiation dose grid 312:

$$D_{accum}^i|_{i=1}^m = D_{actual-fixed}^i + \Sigma_{j=1}^n D_{warped}^{i,j}$$

In that expression, the first term on the right represents the actual radiation dose at the ith landmark point 306 in the fixed image data set. The second term on the right represents the summation of the warped radiation doses at the ith landmark point 306 in the fixed image data as transformed from the n moving image data sets 312.

In step 340 of the method 300, the difference between the actual total point dose $D_{actual-total}^i$ and the accumulated point dose $D_{accum}^i$ is determined for each one of the m landmark points 306 in the fixed image radiation dose grid 310. This calculation results in a set of "accumulated dose errors" 342, with one error value corresponding to each one of the m landmark points 306 in the fixed image radiation dose grid 310. This set of accumulated dose errors may thus be represented by the short-hand $D_{accum-error}^i$, wherein $$D_{accum-error}^i|_{i=1}^m = D_{actual-total}^i - D_{accum}^i.$$

The set 342 of accumulated dose errors $D_{accum-error}^i$ may then be further manipulated, and/or visualized, in any one of many different manners as already described above in connection with the set 230 of dose errors $D_{error}^i$.

Although not shown in FIGS. 3A and 3B, the method 300 may be easily modified to handle situations where there is more than one fixed image data set. That is, in these cases, there is more than one image data set which was originally acquired in the common frame of reference to which all imaging data sets are to be transformed. In such situations, the fixed image radiation dose grid 210 may simply be modified so that each voxel in the grid 210 reflects the summation of the radiation doses as recorded in each one of the multiple fixed image data sets.

As discussed above, in steps 204 and 304 of the respective methods 200 and 300, corresponding landmark points 206 or 306 in the fixed image and in the moving image are identified. In one embodiment, the identification may be made manually, but that process can be tedious and difficult in practice. Thus, in alternative embodiments, the landmark identification steps 204 and 304 may advantageously be automated or semi-automated.

Figure 4:
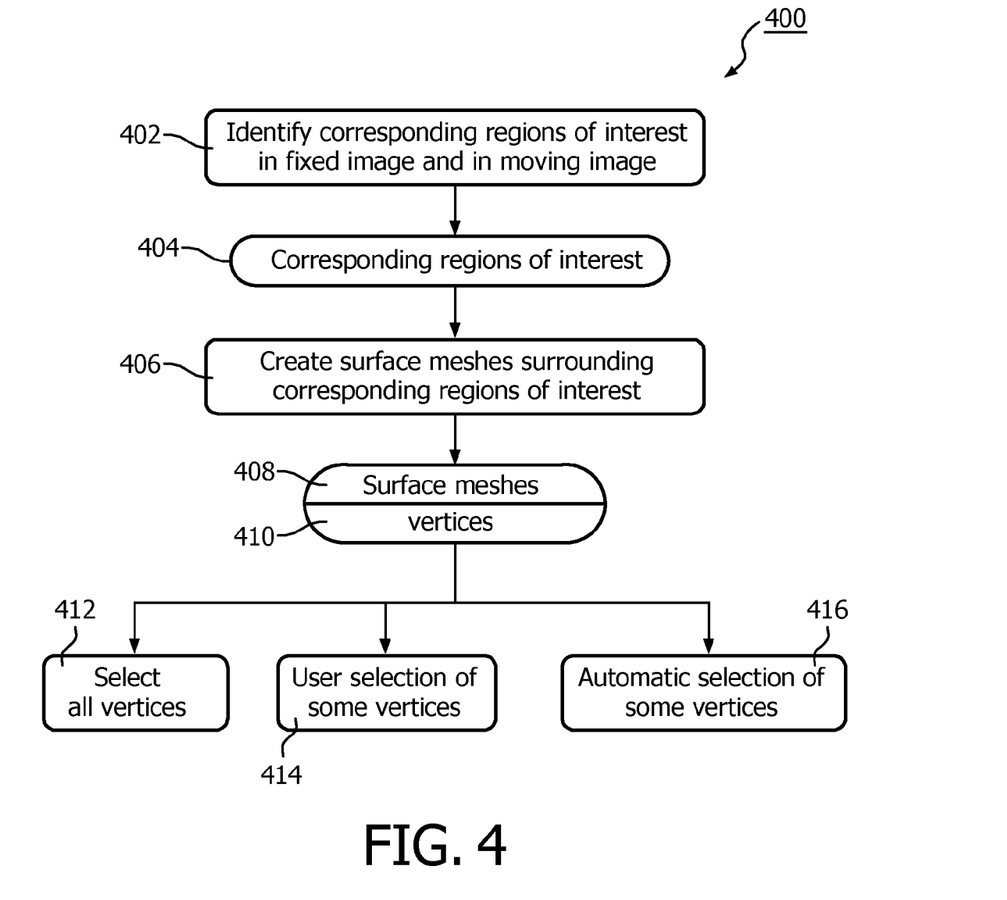
FIG. 4 illustrates a method 400 for automatically or semi-automatically identifying landmark points during implementation of either method 200 or 300.

FIG. 4 illustrates one exemplary method 400 for automatically or semi-automatically identifying landmark points in the fixed image and in the moving image. The method 400 may be implemented by a radiation treatment therapy planning system, such as the module 112. The illustrated exemplary method 400 contains several steps. Further embodiments of a suitable method for identifying landmark points may include other additional steps, or omit one or more of the steps in the illustrated method 400. Also, the order in which the process flows herein have been described is not critical and can be rearranged while still accomplishing the same results. Thus the process flows described herein may be rearranged, consolidated, and/or re-organized in their implementation as warranted or desired.

In step 402 of the method 400, corresponding regions of interest 404 are identified in the fixed image data set and in the moving image data set. The corresponding regions of interest 404 may be, for example, the same anatomical structure or structures in the fixed image data set and in the moving image data set. Thus, one or more of the patient's heart, rib bones, lungs, liver, or other anatomical structures may be identified as the corresponding regions of interest. In further embodiments, the definition 402 of the corresponding regions of interest 404 may be unrelated to the anatomical structures being imaged. Regardless of how the corresponding regions of interest 404 are defined, however, they should be defined in the same way in the fixed image data set and in the moving image data set. This identification 402 can be made manually or automatically. Automated segmentation tools are well known in the art, such as for example deformable propagation, auto/atlas segmentation, model based segmentation, and the like.

In step 406 of the method 400, a radiation treatment planning system such as the module 112 creates surface meshes 408 approximating each one of the corresponding regions of interest 404. This may be accomplished, for example, by shrink-fitting the meshes 408 to the regions of interest 404. The surface meshes 408 are composed of multiple flat surfaces which intersect each other at edges and at vertices 410. The surface meshes 408 surrounding corresponding regions of interest 404 between the two image data sets have the same number of vertices 410. However, they may differ in the relative locations of the vertices 410.

Thus, in one embodiment, a fixed image surface mesh $408_f$ having m vertices 410 is created to approximate the region of interest $404_f$ in the fixed image. There are many conventional methods of generating such an approximation surface mesh. The fixed image surface mesh $408_f$ is then copied over into the moving image data set and modified to become a moving image surface mesh $408_m$, which approximates the corresponding region of interest $404_m$ in the moving image. The surface mesh modifications are limited to moving each one of the faces of the mesh in or out along an axis which is normal to the face. For example, the modifications may be made by determining a minimum or maximum energy value associated with deforming the surface mesh to approximate the region of interest $404_m$. The resulting surface meshes $408_f$ and $408_m$ will then have the same number (m) of vertices 410, and the same shape(s) of surfaces between the vertices 410. This fitting process may of course be reversed, and start with a moving image surface mesh $408_m$.

The corresponding vertices 410 between the two surface meshes 408$_f$ and 408$_m$ are then used as candidates for becoming 204 or 304 landmark points 206 or 306 in the remaining steps of the method 200 or 300 above. In one embodiment of the method 400, in step 412, each one of the corresponding vertices 410 is selected as a landmark point. In another embodiment of the method, a sub-set of the vertices 410 may be selected as the landmark points, such as illustrated at steps 414 and 416.

Thus, the user may be given the option 414 to select a sample of corresponding surface mesh vertices 410 to use as landmarks 206 or 306. This user selection 414 can be done using any number of methods. In one embodiment, the user may select the surface mesh vertex landmarks 206 by interacting with the radiation treatment planning system 112 using a display 114 and an input device 116. The display 114 may show the imaging data in either two dimensions or three dimensions. In a first example, the user may use the input device 116 to identify individual mesh vertices 410 to be used as landmarks 206 or 306. In a second example, the user may use the input device 116 to identify an entire region of the imaging data such as by creating a bounding box or other shape on the display 114, so that all the mesh vertices 410 located within that identified region are used as landmarks 206 or 306. In a third example, the user may simply select corresponding mesh vertices from a list such as a spreadsheet.

In other embodiments, a sub-set of mesh vertices 206 or 306 may be selected automatically without user intervention, as illustrated at step 416. This automatic selection 416 can be done using any number of methods. In one embodiment, the radiation treatment planning system 112 selects every other vertex 410 as a landmark 206 or 306, or every third vertex 410, or every fourth vertex 410, etc. In other embodiments, the radiation treatment planning system 112 may select mesh vertices 410 which are located in regions of high curvature, or in regions where target structures and non-target structures overlap, or in regions corresponding to other identifying features of the surface mesh 408.

Or, a combination of user selection 414 and automatic selection 416 of corresponding mesh vertices 410 may be performed. In one example, an initial automatic selection 416 of vertices 410 may be performed, followed by a user selection 414 which either adds or deletes vertices 410 from the initial selection.

The invention has been described with reference to the several embodiments. Obviously, modifications and alterations will occur to others upon reading and understanding the preceding detailed description. For example, the methods 200 and 300 may be utilized to compare and contrast two or more different transformation matrices. It is intended that the invention be construed as including all such modifications and alterations insofar as they come within the scope of the appended claims or the equivalents thereof. The invention may take form in various compositions, components and arrangements, combinations and sub-combinations of the elements of the disclosed embodiments.

Having thus described several embodiments, the invention is now claimed to be:

1. A method for determining a radiation dose transformation error, wherein there is a deformation in one or more imaged structures as recorded by at least one fixed image data set and at least one moving image data set, the method comprising:
    automatically or semi-automatically identifying corresponding landmark points in the fixed image and in the moving image;
    obtaining a fixed image radiation dose grid and a moving image radiation dose grid, wherein the moving image radiation dose grid comprises actual moving image point doses representing radiation dose levels at the landmark points in the moving image radiation dose grid;
    determining a transformation matrix between the fixed image and the moving image;
    applying the transformation matrix to the moving image data set to generate a warped radiation dose grid;
    determining warped point doses representing radiation dose levels in the warped radiation dose grid at the landmark points in the fixed image radiation dose grid; and
    determining a difference between the actual point dose and the warped point dose at corresponding landmark points in order to generate dose errors.

2. The method of claim 1, wherein the fixed image data set and the moving image data set are of a same person taken at different times.

3. The method of claim 1, wherein the fixed image data set and the moving image data set are of a same region within different persons.

4. The method of claim 1, further comprised of analyzing the dose errors to generate a composite dose error which is representative of the dose errors.

5. The method of claim 4, wherein analyzing the dose errors is limited to a subset of the dose errors.

6. The method of claim 1, further comprised of illustrating the dose errors on a display.

7. The method of claim 6, wherein the illustration comprises one of a color map and an arrow map.

8. The method of claim 1, wherein there is one moving image data set to be transformed to a frame of reference of the fixed image data set.

9. The method of claim 1, wherein there is more than one moving image data set to be transformed to a frame of reference of the fixed image data set.

10. The method of claim 9, wherein the fixed image radiation dose grid comprises actual fixed image point doses representing radiation dose levels at the landmark points in the fixed image radiation dose grid, and determining the dose errors further comprises:
    determining, for each one of the moving image data sets:
        a moving image radiation dose grid, wherein the moving image radiation dose grid comprises actual moving image point doses representing radiation dose levels at the landmark points in the moving image radiation dose grid;
        a transformation matrix between the fixed image and the moving image; and
        a warped radiation dose grid, resulting from applying the transformation matrix to the moving image data set, and comprising warped point doses representing radiation dose levels in the warped radiation dose grid at the landmark points in the fixed image radiation dose grid; and
    calculating an actual point dose for each of the landmark points, comprising a summation of the actual fixed image point dose at a fixed landmark point and each one of the actual moving image point doses at moving landmark points which correspond to the fixed landmark point;
    calculating an accumulated point dose for each of the landmark points in the fixed image radiation dose grid, comprising a summation of the actual fixed image point dose and each one of the warped point doses from the landmark point; and determining a difference between the actual point dose and the accumulated point dose at each landmark in the fixed image radiation dose grid in order to generate dose errors.

11. The method of claim 10, wherein there is more than one fixed image data set, and the actual fixed image point doses equal a summation of radiation doses recorded in each of the more than one fixed image data sets.

12. A system for determining a radiation dose transformation error, wherein there is a deformation in one or more imaged structures as recorded by at least one fixed image data set and at least one moving image data set, the system including a non-transitory computer readable medium comprising logic to:

automatically or semi-automatically identify corresponding landmark points in the fixed image and in the moving image;

obtain a fixed image radiation dose grid and a moving image radiation dose grid, wherein the moving image radiation dose grid comprises actual moving image point doses representing radiation dose levels at the landmark points in the moving image radiation dose grid;

determine a transformation matrix between the fixed image and the moving image; apply the transformation matrix to the moving image data set to generate a warped radiation dose grid;

determine warped point doses representing radiation dose levels in the warped radiation dose grid at the landmark points in the fixed image radiation dose grid; and determine a difference between the actual point dose and the warped point dose at corresponding landmark points in order to generate dose errors.

13. The system of claim 12, wherein the computer readable medium further comprises logic to analyze the dose errors to generate a composite dose error which is representative of the dose errors.

14. The system of claim 12, wherein the computer readable medium further comprises logic to illustrate the dose errors on a display.

15. The system of claim 12, wherein there is more than one moving image data set to be transformed to a frame of reference of the fixed image data set.

16. The system of claim 15, wherein the fixed image radiation dose grid comprises actual fixed image point doses representing radiation dose levels at the landmark points in the fixed image radiation dose grid, and wherein the computer readable medium further comprises logic to:

determine, for each one of the moving image data sets:
a moving image radiation dose grid, wherein the moving image radiation dose grid comprises actual moving image point doses representing radiation dose levels at the landmark points in the moving image radiation dose grid;

a transformation matrix between the fixed image and the moving image; and a warped radiation dose grid, resulting from applying the transformation matrix to the moving image data set, and comprising warped point doses representing radiation dose levels in the warped radiation dose grid at the landmark points in the fixed image radiation dose grid; and calculate an actual point dose for each of the landmark points, comprising a summation of the actual fixed image point dose at a fixed landmark point and each one of the actual moving image point doses at moving landmark points which correspond to the fixed landmark point;

calculate an accumulated point dose for each of the landmark points in the fixed image radiation dose grid, comprising a summation of the actual fixed image point dose and each one of the warped point doses from the landmark point; and determine a difference between the actual point dose and the accumulated point dose at each landmark in the fixed image radiation dose grid in order to generate dose errors.

17. The system of claim 16, wherein there is more than one fixed image data set, and the actual fixed image point doses equal a summation of radiation doses recorded in each of the more than one fixed image data sets.

* * * * *